United States Patent
Zhong et al.

(10) Patent No.: US 10,561,143 B2
(45) Date of Patent: Feb. 18, 2020

(54) FUNGICIDAL COMPOSITION HAVING SYNERGISTIC EFFECT

(71) Applicant: JIANGSU HUIFENG AGROCHEMICAL CO., LTD., Dafeng, Jiangsu (CN)

(72) Inventors: Hangen Zhong, Dafeng (CN); Hongjin Ji, Dafeng (CN)

(73) Assignee: JIANGSU HUIFENG AGROCHEMICAL CO., LTD., Jiangsu (CN)

(*) Notice: Subject to any disclaimer, the term of this patent is extended or adjusted under 35 U.S.C. 154(b) by 168 days.

(21) Appl. No.: 14/897,179

(22) PCT Filed: Jul. 9, 2013

(86) PCT No.: PCT/CN2013/079078
§ 371 (c)(1),
(2) Date: Dec. 9, 2015

(87) PCT Pub. No.: WO2014/198079
PCT Pub. Date: Dec. 18, 2014

(65) Prior Publication Data
US 2016/0135460 A1    May 19, 2016

(30) Foreign Application Priority Data
Jun. 9, 2013  (CN) .......................... 2013 1 0232680

(51) Int. Cl.
| | | |
|---|---|---|
| A61K 31/426 | (2006.01) | |
| A61K 31/428 | (2006.01) | |
| A61K 31/165 | (2006.01) | |
| A61K 31/166 | (2006.01) | |
| A61K 31/167 | (2006.01) | |
| A61K 31/4196 | (2006.01) | |
| A61K 31/4402 | (2006.01) | |
| A01N 43/80 | (2006.01) | |
| A01N 25/14 | (2006.01) | |
| A01N 37/20 | (2006.01) | |
| A01N 43/40 | (2006.01) | |
| A01N 43/50 | (2006.01) | |
| A01N 43/56 | (2006.01) | |
| A01N 43/653 | (2006.01) | |
| A01N 43/76 | (2006.01) | |
| A01N 47/12 | (2006.01) | |

(52) U.S. Cl.
CPC ............ *A01N 43/80* (2013.01); *A01N 25/14* (2013.01); *A01N 37/20* (2013.01); *A01N 43/40* (2013.01); *A01N 43/50* (2013.01); *A01N 43/56* (2013.01); *A01N 43/653* (2013.01); *A01N 43/76* (2013.01); *A01N 47/12* (2013.01)

(58) Field of Classification Search
CPC ............... A61K 31/426; A61K 31/428; A61K 31/165–167; A61K 31/4196; A61K 31/4402
See application file for complete search history.

(56) References Cited

FOREIGN PATENT DOCUMENTS

| CN | 101796955 A |   | 8/2010 |
| CN | 102172240 A | * | 9/2011 |
| CN | 102763657 A |   | 11/2012 |

OTHER PUBLICATIONS

Li et al. CN102172240A. (dated Sep. 7, 2011). English translation.*
Damicone et al. ("Oklahoma Cooperative Extension Service—EPP-7663". Fungicide Resistance Management. Division of Agricultural Sciences and Natural Resources. Oklahoma State University. https://web.archive.org/web/20130202190338/http://pods.dasnr.okstate.edu/docushare/dsweb/Get/Document-2317/F-7663web.pdf: 8 pages).*
Leadbeater, "Resistance Risk to Qol Fungicides and Anti-Resistance Strategies." Fungicide Resistance in Crop Protection. Risk and Management. Edited by T Thind, Punjab Agricultural University, India. 2012. pp. 141-142. (Year: 2012).*
Mar. 13, 2014 International Search Report issued in International Patent Application No. PCT/CN2013/079078.

* cited by examiner

*Primary Examiner* — Rachael E Bredefeld
*Assistant Examiner* — Chris E Simmons
(74) *Attorney, Agent, or Firm* — Oliff PLC

(57) ABSTRACT

A fungicidal composition having a synergistic effect is provided. The composition including active ingredients A and B. The active ingredient A is benziothiazolinone, the active ingredient B is one selected from benthiavalicarb-isopropyl, zoxamide, prothioconazole, boscalid, fenamidone, fluopicolide, famoxadone, pyraclostrobin, picoxystrobin or fluazinam, and the weight ratio of the two ingredients is from 1:50 to 50:1. The test results show that the fungicidal composition according to the present invention has an obvious synergistic effect, such that the application rate is reduced and the cost is lowered; and is useful in controlling certain particular fungal diseases on grain crops, vegetables, and fruits with a broadened fungicidal spectrum, a retarded resistance development of the fungi, and an improved control effect.

17 Claims, No Drawings

FUNGICIDAL COMPOSITION HAVING SYNERGISTIC EFFECT

BACKGROUND

Technical Field

The present invention belongs to the field of agricultural plant protection, and particularly relates to a fungicidal composition with improved performances, and more particularly to a fungicidal composition comprising benziothiazolinone.

Related Art

Benziothiazolinone is a new broad-spectrum fungicide, which is mainly used for controlling and treating various bacterial and fungal diseases on cereal crops, vegetables, and fruits. The mechanisms of fungicidal action mainly include destroying the nuclei structure of the harmful fungi to cause they to die due to lose of the core component, and interfering with the metabolism of the fungal cells to cause physiological disturbance, thus ultimately leading to death. When the agent is used in the early stage of disease development, the plants may be effectively protected against infection of pathogens; and when the agent is used in an appropriately increased amount after the disease is developed, the spread of the harmful fungi is considerably controlled, thus achieving dual actions of protection and eradication.

Benthiavalicarb-isopropyl has a strong preventive, curative, and penetration activity, and has a good persistence and rainfastness. In field trials, benthiavalicarb-isopropyl can effectively control the late blight of potatoes and tomatoes and the downy mildew of grape and other crops at a low application rate. When mixed with other fungicides, benthiavalicarb-isopropyl also has a quite good efficacy for harmful fungi.

Zoxamide is a new broad-spectrum fungicide, which is mainly used for controlling and treating various bacterial and fungal diseases including downy mildew on cucumbers, black spot on pears, scab on apples, anthracnose on citrus, anthracnose on grapes, and others. The mechanisms of fungicidal action mainly include destroying the nuclei structure of the harmful fungi to cause they to die due to lose of the core component, and interfering with the metabolism of the fungal cells to cause physiological disturbance, thus ultimately leading to death.

Prothioconazole is a new broad-spectrum triazolthione fungicide developed by Bayer Company, which is mainly used for controlling numerous diseases of cereals, wheat and barley, beans and other crops. Prothioconazole has a low toxicity, no teratogenicity and mutagenicity, and is non-toxic to embryos and safe for human and environment. The mechanism of action is inhibiting the demethylation at position 14 of lanosterol or 2,4-methylene dihydrolanosterol that is a precursor of sterol in fungi.

Fenamidone has similar mechanism of action and features to those of famoxadone and methoxyacrylate fungicides, that is, through inhibition of the mitochondrial respiration by hindering the electron transfer at coenzyme Q for hydrogenation-cytochrome C oxidoreductase level. Fenamidone is applicable to wheat, cotton, grape, tobacco, turf, sunflower, rose, potato, tomato, and other vegetables for controlling various diseases including downy mildew, blight, *phytophthora* blight, damping-off, black spot, and mottled rot.

Pyraclostrobin is a new broad-spectrum fungicide. The mechanism of action includes inhibition of the mitochondrial respiration by hindering the electron transfer during cytochrome synthesis. Pyraclostrobin has protective, curative, and leaf-penetrating translocation effects. The field efficacy test results show that the pyraclostrobin concentrate has a good control effect on powdery mildew and downy mildew of cucumber and black spot and leaf spot of bananas.

Picoxystrobin is a systemic broad-spectrum fungicide, which is mainly used for controlling leaf diseases of wheat and barley, for example, leaf blight, leaf rust, glume blight, brown spot, and powdery mildew. Compared with other methoxyacrylate fungicides, picoxystrobin has a more potent curative effect for leaf blight, net blotch, and leaf blotch of wheat.

Fluazinam is a 2,6-dinitroaniline protective fungicide, which can control the disease caused by *Botrytis cinerea* when applied at a dosage of 50-100 g (a.i.)/100 L. Fluazinam is quite effective for *Alternaria* spp, *Botrytis* spp, *Phytophthora* spp, *Plasmopara* spp, *Sclerotinia* spp, and *Nigrospora* spp, is highly effective for *Botrytis cinerea* resistant to benzimidazole and dicarboximide fungicides, and has long persistence and good rainfastness. Moreover, fluazinam also has a good control effect for phytophagous mites, crucifer club root, and rice damping-off caused by *Rhizopus* spp.

Boscalid is a new nicotinamide fungicide, which is broad in fungicidal spectrum, active for almost all the types of harmful fungi, highly effective for controlling powdery mildew, grey mold, selerotium blight and various rots, and effective for fungi resistant to other agents. Boscalid is mainly used for controlling harmful fungi on rape, grape, fruit trees, vegetables and field crops.

Fluopicolide has a prominent control effect on downy mildew, blight, late blight, damping-off and other common diseases caused by fungi from Oomycetes, is safe for crops and environment, and particularly useful in production of high-quality and green vegetables. Fluopicolide has a highly potent protective and curative effect for diseases on vegetables caused by fungi from Oomycetes due to its unique formulation. Fluopicolide has excellent systemic translocation performance and high thin layer penetrating ability, and has potent inhibition on all the major morphologies of the pathogens, thus providing full and persistent protection for young leaves, stems, tubers, and young fruits. Because fluopicolide can be absorbed quickly through the leaf surface, it has a good rainfastness, thus provide a reliable safeguard for disease control of vegetables in the rain season.

Famoxadone is a new high-potent and broad-spectrum fungicidal agent, which is suitably used for wheat, barley, peas, sugar beets, rape, grape, potato, melons, hot peppers, tomato, and other crops, and mainly used for controlling diseases caused by fungi from Ascomycetes, Basidiomycetes, and Oomycetes, for example, powdery mildew, rust, glume blight, net blotch, downy mildew, and late blight.

It is showed in practical use of pesticides that the repeated and exclusive application of one active compound to control the harmful fungi will result in the occurrence of rapid selectivity of the fungus strain in most cases. At present, the harmful fungi are controlled by using mixtures of compounds with different activities for the purpose of reducing the hazard of the selectivity of the resistant fungus strain. By combining active compounds having different mechanisms of action, the resistance development can be slowed down, the application rate is reduced, and thus the control cost is lowered.

SUMMARY

In view of the technical problems above of resistance and persistence in soil of the fungicides in practical use, two fungicides of different mechanisms of fungicidal action are screened out and combined, to improve the control effect of the fungicides, retard the resistance development, reduce the application rate, and lower the control cost.

To solve the above technical problems, the present invention provides a fungicidal composition. The composition comprises active ingredients A and B. The active ingredient A is benziothiazolinone, the active ingredient B is one selected from benthiavalicarb-isopropyl, zoxamide, prothioconazole, boscalid, fenamidone, fluopicolide, famoxadone, pyraclostrobin, picoxystrobin or fluazinam. The inventors find through tests that the fungicidal composition has an obvious synergistic effect, and importantly, the application rate is reduced, such that the cost is lowered. The ingredients A and B have different chemical structures and distinct mechanisms of action, by which the fungicidal spectrum can be broadened and the occurrence and development rate of resistance of the pathogens can be delayed to some extent when combined. Moreover, the ingredients A and B have no cross resistance.

In the fungicidal composition, the weight ratio of the ingredient A to the ingredient B is from 1:50-50:1, and preferably 1:30-30:1, and more preferably 1:20-20:1 or 1:10-30:1 and most preferably 1:10-10:1 to achieve a much significant synergistic effect.

The fungicidal composition according to the present invention comprises 5-85% by weight of the active ingredient and 95-15% by weight of pesticide adjuvants. Further, the composition is prepared into pesticidally acceptable formations with the active ingredients and the pesticide adjuvants.

The present invention provides use of the fungicidal composition comprising the ingredient A (benziothiazolinone) and the ingredient B (benthiavalicarb-isopropyl, zoxamide, prothioconazole, boscalid, fenamidone, fluopicolide, famoxadone, pyraclostrobin, picoxystrobin, or fluazinam) in the control of diseases on crops in the agricultural area.

When used in controlling the diseases on crops, the fungicidal composition of the present invention may be optionally used for seed impregnation, sprayed onto the leaves by reconstitution with water during the growth period of the crops, or applied onto the surface of the target objects, depending on the different diseases to be controlled.

The composition may further comprise a carrier, an adjuvant and/or a surfactant. A commonly used adjuvant may be blended during application.

The suitable adjuvant may be a solid or liquid that is generally a material commonly used in the preparation of formulations, for example, a natural or regenerated mineral substance, a solvent, a dispersing agent, a wetting agent, an adhesive, a thickener, a binder or a fertilizer.

The composition of the present invention may be applied by administering the composition of the present invention to the aboveground parts of plants, in particular to the leaves or leaf surface thereof. The application frequency and rate depend on the pathogen biology and the climatic and maintenance conditions. The locus where the plant is growing, for example paddy field, may be impregnated with a liquid formulation of the composition, or the composition is incorporated in solid form into the soil, for example, in granular form (soil application) or penetrates the plant through the roots via the soil (systemic action). Alternatively, the occurrence of diseases may be eradicated and prevented by coating or immersing the seeds.

The composition may be used by applying the active ingredients alone or in admixture with additives.

The composition of the present invention may be prepared into various formulations, for example, a wettable powder, a suspension, an oily suspension, water dispersible granules, an aqueous emulsion, or a microemulsion. Depending on the properties of the compositions, the objectives intended to be achieved by applying the compositions, and the environmental conditions, the compositions may be applied by spraying, atomizing, dusting, scattering, or pouring.

The composition of the present invention may be prepared into various formulations through known processes. The active ingredients may be uniformly mixed with an adjuvant such as a solvent or a solid carrier and a surfactant if needed, and ground to prepare a desired formulation.

The solvent may be selected from aromatic hydrocarbons containing preferably 8 to 12 carbon atoms, for example, a xylene mixture, substituted benzene, or a phthalate ester, for example, dibutyl or dioctyl phthalate; aliphatic hydrocarbons, for example, cyclohexane or paraffin; alcohols, glycols and ethers and esters thereof, for example, ethanol, ethylene glycol, and ethylene glycol monomethyl ether; ketones, for example, cyclohexanone; high-polarity solvents, for example, N-methyl-2-pyrrolidone, dimethyl sulfoxide, or dimethyl formamide; and vegetable oils, for example, soy bean oil.

The solid carrier includes for example natural mineral fillers generally used for powders and dispersible powders, for example, talc, kaolin, montmorillonite or activated bauxite. To manage the physical properties of the composition, highly dispersive silicic acid or highly dispersive absorbent polymer carrier may also be added, for example, granular adsorptive carrier or non-adsorptive carrier. The suitable granular adsorptive carrier is porous, for example, pumice, soapy clay or bentonite. The suitable non-adsorptive carrier includes for example calcite or sand. Moreover, a large amount of inorganic or organic material that is pre-prepared into granules and especially dolomite may be used as the carrier.

As desired by the chemical nature of the active ingredients in the composition according to the present invention, the suitable surfactant includes ligninsulfonic acid, naphthalenesulfonic acid, phenolsulfonic acid, alkaline earth metal or amine salts, alkylarylsulfonates, alkylsulfates, alkylsulfonates, fatty alcohol sulfates, fatty acids and ethylene glycol sulfated fatty alcohol ethers, condensation products of sulfonated naphthalene and naphthalene derivatives with formaldehyde, condensation products of naphthalene or naphthalenesulfonic acid with phenol and formaldehyde, polyoxyethylene octyl phenyl ethers, ethoxylated iso-octylphenol, octylphenol, nonylphenol, alkylaryl polyethylene glycol ethers, tributylphenyl polyethylene glycol ether, tristearylphenyl polyethylene glycol ether, alkylaryl polyether alcohols, ethoxylated castor oil, polyoxyethylene alkyl ethers, condensation products of ethylene oxide, ethoxylated polyoxypropylene, polyethylene glycol ether laurate acetal, sorbates, waste lignin sulfite liquor, and methyl cellulose.

The two active ingredients in the fungicidal composition of the present invention have a synergistic effect, such that the activity of the composition is obviously higher than the respective activity or expected sum of the respective activity of single compounds alone. The synergistic effect leads to a reduced application rate, a broadened fungicidal spectrum, fast onset of action, and a prolonged control effect, whereby the fungi harmful to plants can be well controlled only by means of one or several applications, and the underlying application interval is widened. In this application, the above effect is further confirmed through examples of control tests on grape downy mildew, wheat rust, potato late blight, wheat powdery mildew, tomato grey mold, and grape anthracnose respectively. These features are particularly important in practice of controlling the fungi harmful to plants.

The fungicidal composition of the present invention exhibits the following additional features. 1. The composition of the present invention has an obvious synergistic effect. 2. Because the two individual agents in the composition of the present invention have highly different structures and completely different mechanisms of action, no cross resistance exists, such that the problem of resistance development occurred due to the use of single agents alone can be retarded. 3. The composition of the present invention is safe for crops, and good in the control effect. It is demonstrated through tests that the fungicidal composition of the present invention has stable chemical properties and a significant synergistic effect since the two active ingredients therein exhibit an obvious synergistic and complementary effect on the target organisms.

DETAILED DESCRIPTION

To make the objectives, technical solutions, and advantages of the present invention clearer, the present invention is described in further detail with reference to examples. It should be understood that specific examples described herein are merely provided for explaining, instead of limiting, the present invention. Any modifications, equivalent replacements, and improvements made without departing from the spirit and principle of the present invention fall within the protection scope of the present invention.

The percentages given in all the formulations in the examples below are all weight percentages. The various formulations are processed from the composition of the present invention by a process known in the prior art which may be varied as desired.

I. Preparation Example of Formulations

The formulations processed from the fungicidal composition of the present invention are those known in the prior art. For intuitively and clearly show the synergistic effect between the active ingredients of the present invention, only the wettable powder is optionally prepared in the preparation examples of formulations and used as the pesticide formulation to validate the synergistic effect between the active ingredients.

The active ingredients benziothiazolinone and one of benthiavalicarb-isopropyl, zoxamide, prothioconazole, boscalid, fenamidone, fluopicolide, famoxadone, pyraclostrobin, picoxystrobin or fluazinam were fully mixed with various adjuvants and fillers in proportion, and ground by an ultra-fine grinder, to obtain a wettable powder.

Example 1: 62% Benziothiazolinone•Benthiavalicarb-Isopropyl Wettable Powder benziothiazolinone 60%, benthiavalicarb-isopropyl 2%, a sodium alkyl naphthalene sulfonate 4%, sodium dodecyl sulfonate 3%, ammonium sulfate 3%, and light calcium carbonate q.s. to 100%.

Example 2: 50% Benziothiazolinone•Benthiavalicarb-Isopropyl Wettable Powder benziothiazolinone 25%, benthiavalicarb-isopropyl 25%, sodium lignin sulfonate 6%, sodium dodecyl sulfonate 3%, xanthan gum 1%, sodium carboxymethyl starch 1%, and attapulgite clay q.s. to 100%.

Example 3: 65% Benziothiazolinone•Benthiavalicarb-Isopropyl Wettable Powder benziothiazolinone 2%, benthiavalicarb-isopropyl 63%, sodium lignin sulfonate 5%, a sodium methylnaphthalene sulfonate formaldehyde condensate 7%, sodium dodecyl sulfate 3%, and diatomaceous earth q.s. to 100%

Example 4: 85% Benziothiazolinone•Zoxamide Wettable Powder benziothiazolinone 83%, zoxamide 2%, ammonium sulfate 1%, sodium alginate 2%, a sodium methylnaphthalene sulfonate formaldehyde condensate 1%, organic silicone 1%, and bentonite q.s. to 100%

Example 5: 30% Benziothiazolinone•Zoxamide Wettable Powder benziothiazolinone 15%, zoxamide 15%, sodium dodecyl sulfonate 2%, a sodium alkyl naphthalene sulfonate 2%, ammonium sulfate 3%, and light calcium carbonate q.s. to 100%.

Example 6: 75% Benziothiazolinone•Zoxamide Wettable Powder benziothiazolinone 2%, zoxamide 73%, a sodium methylnaphthalene sulfonate formaldehyde condensate 5%, sodium lignin sulfonate 4%, sodium dodecyl sulfate 3%, and diatomaceous earth q.s. to 100%.

Example 7: 62% Benziothiazolinone•Prothioconazole Wettable Powder benziothiazolinone 60%, prothioconazole 2%, sodium carboxymethyl starch 1%, sodium dodecyl sulfonate 4%, sodium lignin sulfonate 4%, xanthan gum 1%, and attapulgite clay q.s. to 100%.

Example 8: 40% Benziothiazolinone•Prothioconazole Wettable Powder benziothiazolinone 20%, prothioconazole 20%, ammonium sulfate 1%, sodium alginate 2%, a sodium methylnaphthalene sulfonate formaldehyde condensate 1%, organic silicone 1%, and bentonite q.s. to 100%.

Example 9: 65% Benziothiazolinone•Prothioconazole Wettable Powder benziothiazolinone 2%, prothioconazole 63%, a sodium methylnaphthalene sulfonate formaldehyde condensate 5%,

Example 10: 65% Benziothiazolinone·Boscalid Wettable Powder benziothiazolinone 63%, boscalid 2%, calcium lignin sulfonate 2%, sodium dodecylbenzene sulfonate 1%, bentonite 2%, and attapulgite clay q.s. to 100%.

Example 11: 60% Benziothiazolinone·Boscalid Wettable Powder benziothiazolinone 30%, boscalid 30%, an alkylpolyoxyethylene ether sulfonate 1%, nekal 2%, bentonite 1.5%, white carbon black 2%, and diatomaceous earth q.s. to 100%.

Example 12: 62% Benziothiazolinone·Boscalid Wettable Powder benziothiazolinone 2%, boscalid 60%, a sodium alkylsulfonate 6%, sodium lignin sulfonate 6%, white carbon black 5%, and kaolin q.s. to 100%.

Example 13: 62% Benziothiazolinone·Fenamidone Wettable Powder benziothiazolinone 60%, fenamidone 2%, a polyoxyethylene octyl phenyl ether 2%, sodium lignin sulfonate 6%, white carbon black 4%, and diatomaceous earth q.s. to 100%.

Example 14: 50% Benziothiazolinone·Fenamidone Wettable Powder benziothiazolinone 25%, fenamidone 25%, calcium lignin sulfonate 7%, white carbon black 5%, sodium dodecylbenzene sulfonate 3%, and attapulgite clay q.s. to 100%.

Example 15: 62% Benziothiazolinone·Fenamidone Wettable Powder benziothiazolinone 2%, fenamidone 60%, calcium lignin sulfonate 5%, bentonite 4%, a polyoxyethylene octyl phenyl ether 3%, and attapulgite clay q.s. to 100%.

Example 16: 65% Benziothiazolinone·Fluopicolide Wettable Powder benziothiazolinone 63%, fluopicolide 2%, a polyoxyethylene octyl phenyl ether 1%, sodium lignin sulfonate 2%, white carbon black 3%, and diatomaceous earth q.s. to 100%.

Example 17: 50% Benziothiazolinone·Fluopicolide Wettable Powder benziothiazolinone 25%, fluopicolide 25%, sodium dodecylbenzene sulfonate 3%, white carbon black 5%, calcium lignin sulfonate 7%, and attapulgite clay q.s. to 100%.

sodium lignin sulfonate 4%, sodium dodecyl sulfate 3%, and diatomaceous earth q.s. to 100%.

Example 18: 65% Benziothiazolinone·Fluopicolide Wettable Powder benziothiazolinone 3%, fluopicolide 62%, calcium lignin sulfonate 5%, bentonite 4%, a polyoxyethylene octyl phenyl ether 3%, and attapulgite clay q.s. to 100%.

Example 19: 60% Benziothiazolinone·Famoxadone Wettable Powder benziothiazolinone 58%, famoxadone 2%, sodium dodecylbenzene sulfonate 2%, bentonite 1%, calcium lignin sulfonate 2%, and attapulgite clay q.s. to 100%.

Example 20: 50% Benziothiazolinone·Famoxadone Wettable Powder benziothiazolinone 25%, famoxadone 25%, sodium lignin sulfonate 6%, an alkylsulfonate 6%, white carbon black 11%, and kaolin q.s. to 100%.

Example 21: 60% Benziothiazolinone·Famoxadone Wettable Powder benziothiazolinone 2%, famoxadone 58%, nekal 1%, an alkylpolyoxyethylene ether sulfonate 2%, bentonite 1.5%, white carbon black 2%, and diatomaceous earth q.s. to 100%.

Example 22: 62% Benziothiazolinone·Pyraclostrobin Wettable Powder benziothiazolinone 60%, pyraclostrobin 2%, a sodium alkyl naphthalene sulfonate 4%, sodium dodecyl sulfonate 3%, ammonium sulfate 3%, and light calcium carbonate q.s. to 100%.

Example 23: 50% Benziothiazolinone·Pyraclostrobin Wettable Powder benziothiazolinone 25%, pyraclostrobin 25%, sodium lignin sulfonate 6%, sodium dodecyl sulfonate 3%, xanthan gum 1%, sodium carboxymethyl starch 1%, and attapulgite clay q.s. to 100%.

Example 24: 65% Benziothiazolinone·Pyraclostrobin Wettable Powder benziothiazolinone 2%, pyraclostrobin 63%, sodium lignin sulfonate 5%, a sodium methylnaphthalene sulfonate formaldehyde condensate 7%, sodium dodecyl sulfate 3%, and diatomaceous earth q.s. to 100%.

Example 25: 65% Benziothiazolinone·Picoxystrobin Wettable Powder benziothiazolinone 63%, picoxystrobin 2%, sodium alginate 3%, ammonium sulfate 2%, a sodium methylnaphthalene sulfonate formaldehyde condensate 1%, organic silicone 1%, and bentonite q.s. to 100%.

Example 26: 30% Benziothiazolinone•Picoxystrobin Wettable Powder benziothiazolinone 15%, picoxystrobin 15%, sodium dodecyl sulfonate 2%, a sodium alkyl naphthalene sulfonate 2%, ammonium sulfate 3%, and light calcium carbonate q.s. to 100%.

Example 27: 75% Benziothiazolinone•Picoxystrobin Wettable Powder benziothiazolinone 2%, picoxystrobin 73%, a sodium methylnaphthalene sulfonate formaldehyde condensate 5%, sodium lignin sulfonate 4%, sodium dodecyl sulfate 3%, and diatomaceous earth q.s. to 100%.

Example 28: 62% Benziothiazolinone•Fluazinam Wettable Powder benziothiazolinone 60%, fluazinam 2%, ammonium sulfate 3%, sodium carboxymethyl starch 1%, sodium dodecyl sulfonate 4%, sodium lignin sulfonate 4%, xanthan gum 1%, and attapulgite clay q.s. to 100%.

Example 29: 40% Benziothiazolinone•Fluazinam Wettable Powder benziothiazolinone 20%, fluazinam 20%, ammonium sulfate 1%, sodium alginate 2%, a sodium methylnaphthalene sulfonate formaldehyde condensate 1%, organic silicone 1%, and bentonite q.s. to 100%.

Example 30: 75% Benziothiazolinone•Fluazinam Wettable Powder benziothiazolinone 2%, fluazinam 73%, a sodium methylnaphthalene sulfonate formaldehyde condensate 5%, sodium lignin sulfonate 4%, sodium dodecyl sulfate 3%, and diatomaceous earth q.s. to 100%.

II. Efficacy Test

(I) Bioassay Examples

1. Toxicity test of benziothiazolinone combined respectively with benthiavalicarb-isopropyl, zoxamide, prothioconazole, boscalid, fenamidone, fluopicolide, famoxadone, pyraclostrobin, picoxystrobin, and fluazinam on downy mildew pathogens of grape Test target organisms: downy mildew pathogens of grape Based on the test grade scale, the disease development on the leaves of the whole grape plant was investigated, and the disease index and control effect were calculated.

The control effect was converted into probability (y), the concentration of the agents (μg/ml) in solution was converted into a logarithmic value (x), the toxic regression equation and the median inhibition concentration $EC_{50}$ were calculated by least square method, and the toxicity index and the co-toxicity coefficient (CTC) of the agents were calculated by SUN Peiyun method.

$$\text{Actual toxicity index (ATI)} = (EC50 \text{ of standard}/EC50 \text{ of test agent})*100$$

$$\text{Theoretical toxicity index (TTI)} = \text{toxicity index of agent } A * \text{percentage content of } A \text{ in the mixture} + \text{toxicity index of agent } B * \text{percentage content of } B \text{ in the mixture}$$

$$\text{Co-toxicity coefficient (CTC)} = [\text{actual toxicity index (ATI) of the mixture}/\text{theoretical toxicity index (TTI) of the mixture}]*100$$

Where CTC≤80, the composition exhibits an antagonistic effect; where 80<CTC<120, the composition exhibits an additive effect, and where CTC≥120, the composition exhibits a synergistic effect.

(1) Toxicity Test of Benziothiazolinone Combined with Benthiavalicarb-Isopropyl on Downy Mildew Pathogens of Grape

TABLE 1

Toxicity test result analysis of benziothiazolinone combined with benthiavalicarb-isopropyl on downy mildew pathogens of grape

| Name of agent | $EC_{50}$ (μg/ml) | ATI | TTI | Co-toxicity coefficient (CTC) |
|---|---|---|---|---|
| Benziothiazolinone | 8.92 | 100 | / | / |
| Benthiavalicarb-isopropyl | 10.75 | 82.98 | / | / |
| Benziothiazolinone:benthiavalicarb-isopropyl = 50:1 | 8.12 | 109.85 | 99.666 | 110.218 |
| Benziothiazolinone:benthiavalicarb-isopropyl = 30:1 | 7.28 | 122.53 | 99.451 | 123.206 |
| Benziothiazolinone:benthiavalicarb-isopropyl = 10:1 | 6.32 | 141.14 | 98.452 | 143.359 |
| Benziothiazolinone:benthiavalicarb-isopropyl = 1:1 | 5.83 | 153 | 91.488 | 167.235 |
| Benziothiazolinone:benthiavalicarb-isopropyl = 1:10 | 5.69 | 156.77 | 84.524 | 185.474 |
| Benziothiazolinone:benthiavalicarb-isopropyl = 1:30 | 8.48 | 105.19 | 83.526 | 125.937 |
| Benziothiazolinone:benthiavalicarb-isopropyl = 1:50 | 9.31 | 95.81 | 83.311 | 115.003 |

The results (in Table 1) show that the control effect of the combination of benziothiazolinone with benthiavalicarb-isopropyl on downy mildew of grape is significantly improved, suggesting that the combination has an obvious synergistic effect on downy mildew pathogens of grape.

(2) Toxicity Test of Benziothiazolinone Combined with Zoxamide on Downy Mildew Pathogens of Grape

TABLE 2

Toxicity test result analysis of benziothiazolinone combined with zoxamide on downy mildew pathogens of grape

| Name of agent | $EC_{50}$ (μg/ml) | ATI | TTI | Co-toxicity coefficient (CTC) |
|---|---|---|---|---|
| Benziothiazolinone | 9.41 | 100 | / | / |
| Zoxamide | 11.49 | 81.9 | / | / |
| Benziothiazolinone:zoxamide = 50:1 | 9.16 | 102.73 | 99.645 | 103.096 |
| Benziothiazolinone:zoxamide = 30:1 | 7.63 | 123.33 | 99.416 | 124.054 |
| Benziothiazolinone:zoxamide = 10:1 | 6.51 | 144.55 | 98.354 | 146.969 |
| Benziothiazolinone:zoxamide = 1:1 | 5.59 | 168.34 | 90.949 | 185.093 |
| Benziothiazolinone:zoxamide = 1:10 | 5.93 | 158.68 | 83.543 | 189.938 |
| Benziothiazolinone:zoxamide = 1:30 | 9.22 | 102.06 | 82.481 | 123.738 |
| Benziothiazolinone:zoxamide = 1:50 | 10.15 | 92.71 | 82.252 | 112.715 |

The results (in Table 2) show that the control effect of the combination of benziothiazolinone with zoxamide on downy mildew of grape is significantly improved, suggesting that the combination has an obvious synergistic effect on downy mildew pathogens of grape.

(3) Toxicity Test of Benziothiazolinone Combined with Prothioconazole on Downy Mildew Pathogens of Grape

TABLE 3

Toxicity test result analysis of benziothiazolinone combined with prothioconazole on downy mildew pathogens of grape

| Name of agent | $EC_{50}$ (μg/ml) | ATI | TTI | Co-toxicity coefficient (CTC) |
|---|---|---|---|---|
| Benziothiazolinone | 10.05 | 100 | / | / |
| Prothioconazole | 13.26 | 75.79 | / | / |
| Benziothiazolinone:prothioconazole = 50:1 | 9.51 | 105.68 | 99.525 | 106.184 |
| Benziothiazolinone:prothioconazole = 30:1 | 8.42 | 119.36 | 99.219 | 120.300 |
| Benziothiazolinone:prothioconazole = 10:1 | 6.85 | 146.72 | 97.799 | 150.022 |
| Benziothiazolinone:prothioconazole = 1:1 | 7.19 | 139.78 | 87.896 | 159.029 |
| Benziothiazolinone:prothioconazole = 1:10 | 7.95 | 126.42 | 77.993 | 162.091 |
| Benziothiazolinone:prothioconazole = 1:30 | 10.82 | 92.88 | 76.573 | 121.296 |
| Benziothiazolinone:prothioconazole = 1:50 | 12.15 | 82.72 | 76.267 | 108.461 |

The results (in Table 3) show that the control effect of the combination of benziothiazolinone with prothioconazole on downy mildew of grape is significantly improved, suggesting that the combination has an obvious synergistic effect on downy mildew pathogens of grape.

(4) Toxicity Test of Benziothiazolinone Combined with Boscalid on Downy Mildew Pathogens of Grape

TABLE 4

Toxicity test result analysis of benziothiazolinone combined with boscalid on downy mildew pathogens of grape

| Name of agent | $EC_{50}$ (μg/ml) | ATI | TTI | Co-toxicity coefficient (CTC) |
|---|---|---|---|---|
| Benziothiazolinone | 9.46 | 100 | / | / |
| Boscalid | 11.61 | 81.48 | / | / |
| Benziothiazolinone:boscalid = 50:1 | 9.12 | 103.73 | 99.637 | 104.108 |

TABLE 4-continued

Toxicity test result analysis of benziothiazolinone combined with boscalid on downy mildew pathogens of grape

| Name of agent | $EC_{50}$ (μg/ml) | ATI | TTI | Co-toxicity coefficient (CTC) |
|---|---|---|---|---|
| Benziothiazolinone:boscalid = 30:1 | 7.86 | 120.36 | 99.403 | 121.083 |
| Benziothiazolinone:boscalid = 10:1 | 6.82 | 138.71 | 98.316 | 141.086 |
| Benziothiazolinone:boscalid = 1:1 | 6.87 | 137.7 | 90.741 | 151.751 |
| Benziothiazolinone:boscalid = 1:10 | 7.83 | 120.82 | 83.165 | 145.277 |
| Benziothiazolinone:boscalid = 1:30 | 9.51 | 99.47 | 82.079 | 121.188 |
| Benziothiazolinone:boscalid = 1:50 | 10.62 | 89.08 | 81.845 | 108.840 |

The results (in Table 4) show that the control effect of the combination of benziothiazolinone with boscalid on downy mildew of grape is significantly improved, suggesting that the combination has an obvious synergistic effect on downy mildew pathogens of grape.

(5) Toxicity Test of Benziothiazolinone Combined with Fenamidone on Downy Mildew Pathogens of Grape

TABLE 5

Toxicity test result analysis of benziothiazolinone combined with fenamidone on downy mildew pathogens of grape

| Name of agent | $EC_{50}$ (μg/ml) | ATI | TTI | Co-toxicity coefficient (CTC) |
|---|---|---|---|---|
| Benziothiazolinone | 10.59 | 100 | / | / |
| Fenamidone | 12.78 | 82.86 | / | / |
| Benziothiazolinone:fenamidone = 50:1 | 10.13 | 104.54 | 99.664 | 104.892 |
| Benziothiazolinone:fenamidone = 30:1 | 8.64 | 122.57 | 99.447 | 123.252 |
| Benziothiazolinone:fenamidone = 10:1 | 6.68 | 158.53 | 98.442 | 161.039 |
| Benziothiazolinone:fenamidone = 1:1 | 7.27 | 145.67 | 91.432 | 159.321 |
| Benziothiazolinone:fenamidone = 1:10 | 7.92 | 133.71 | 84.422 | 158.383 |
| Benziothiazolinone:fenamidone = 1:30 | 10.43 | 101.53 | 83.417 | 121.714 |
| Benziothiazolinone:fenamidone = 1:50 | 12.27 | 86.31 | 83.2 | 103.738 |

The results (in Table 5) show that the control effect of the combination of benziothiazolinone with fenamidone on downy mildew of grape is significantly improved, suggesting that the combination has an obvious synergistic effect on downy mildew pathogens of grape.

(6) Toxicity Test of Benziothiazolinone Combined with Fluopicolide on Downy Mildew Pathogens of Grape

TABLE 6

Toxicity test result analysis of benziothiazolinone combined with fluopicolide on downy mildew pathogens of grape

| Name of agent | $EC_{50}$ (μg/ml) | ATI | TTI | Co-toxicity coefficient (CTC) |
|---|---|---|---|---|
| Benziothiazolinone | 12.17 | 100 | / | / |
| Fluopicolide | 15.32 | 79.44 | / | / |
| Benziothiazolinone:fluopicolide = 50:1 | 11.62 | 104.73 | 99.597 | 105.154 |
| Benziothiazolinone:fluopicolide = 30:1 | 10.13 | 120.14 | 99.337 | 120.942 |
| Benziothiazolinone:fluopicolide = 10:1 | 8.74 | 139.24 | 98.131 | 141.892 |
| Benziothiazolinone:fluopicolide = 1:1 | 8.12 | 149.88 | 89.719 | 167.055 |
| Benziothiazolinone:fluopicolide = 1:10 | 8.49 | 143.35 | 81.308 | 176.305 |

TABLE 6-continued

Toxicity test result analysis of benziothiazolinone combined with fluopicolide on downy mildew pathogens of grape

| Name of agent | $EC_{50}$ (μg/ml) | ATI | TTI | Co-toxicity coefficient (CTC) |
|---|---|---|---|---|
| Benziothiazolinone:fluopicolide = 1:30 | 12.18 | 99.92 | 80.102 | 124.741 |
| Benziothiazolinone:fluopicolide = 1:50 | 13.44 | 90.55 | 79.842 | 113.411 |

The results (in Table 6) show that the control effect of the combination of benziothiazolinone with fluopicolide on downy mildew of grape is significantly improved, suggesting that the combination has an obvious synergistic effect on downy mildew pathogens of grape.

(7) Toxicity Test of Benziothiazolinone Combined with Famoxadone on Downy Mildew Pathogens of Grape

TABLE 7

Toxicity test result analysis of benziothiazolinone combined with famoxadone on downy mildew pathogens of grape

| Name of agent | $EC_{50}$ (μg/ml) | ATI | TTI | Co-toxicity coefficient (CTC) |
|---|---|---|---|---|
| Benziothiazolinone | 11.36 | 100 | / | / |
| Famoxadone | 13.81 | 82.26 | / | / |
| Benziothiazolinone:famoxadone = 50:1 | 10.56 | 107.58 | 99.652 | 107.956 |
| Benziothiazolinone:famoxadone = 30:1 | 9.47 | 119.96 | 99.428 | 120.650 |
| Benziothiazolinone:famoxadone = 10:1 | 8.69 | 130.72 | 98.387 | 132.863 |
| Benziothiazolinone:famoxadone = 1:1 | 8.21 | 138.37 | 91.13 | 151.838 |
| Benziothiazolinone:famoxadone = 1:10 | 9.42 | 120.59 | 83.872 | 143.779 |
| Benziothiazolinone:famoxadone = 1:30 | 11.08 | 102.53 | 82.832 | 123.781 |
| Benziothiazolinone:famoxadone = 1:50 | 12.15 | 93.5 | 82.607 | 113.187 |

The results (in Table 7) show that the control effect of the combination of benziothiazolinone with famoxadone on downy mildew of grape is significantly improved, suggesting that the combination has an obvious synergistic effect on downy mildew pathogens of grape.

(8) Toxicity Test of Benziothiazolinone Combined with Pyraclostrobin on Downy Mildew Pathogens of Grape

TABLE 8

Toxicity test result analysis of benziothiazolinone combined with pyraclostrobin on downy mildew pathogens of grape

| Name of agent | $EC_{50}$ (μg/ml) | ATI | TTI | Co-toxicity coefficient (CTC) |
|---|---|---|---|---|
| Benziothiazolinone | 11.85 | 100 | / | / |
| pyraclostrobin | 10.69 | 110.85 | / | / |
| Benziothiazolinone:pyraclostrobin = 50:1 | 10.19 | 116.29 | 100.213 | 116.043 |
| Benziothiazolinone:pyraclostrobin = 30:1 | 9.52 | 124.47 | 100.35 | 124.036 |
| Benziothiazolinone:pyraclostrobin = 10:1 | 7.41 | 159.92 | 100.986 | 158.359 |
| Benziothiazolinone:pyraclostrobin = 1:1 | 7.12 | 166.43 | 105.426 | 157.864 |
| Benziothiazolinone:pyraclostrobin = 1:10 | 8.27 | 143.29 | 109.865 | 130.424 |
| Benziothiazolinone:pyraclostrobin = 1:30 | 8.71 | 136.05 | 110.501 | 123.121 |
| Benziothiazolinone:pyraclostrobin = 1:50 | 10.15 | 116.75 | 110.638 | 105.524 |

The results (in Table 8) show that the control effect of the combination of benziothiazolinone with pyraclostrobin on downy mildew of grape is significantly improved, suggesting that the combination has an obvious synergistic effect on downy mildew pathogens of grape.

(9) Toxicity Test of Benziothiazolinone Combined with Picoxystrobin on Downy Mildew Pathogens of Grape

TABLE 9

Toxicity test result analysis of benziothiazolinone combined with picoxystrobin on downy mildew pathogens of grape

| Name of agent | $EC_{50}$ (μg/ml) | ATI | TTI | Co-toxicity coefficient (CTC) |
|---|---|---|---|---|
| Benziothiazolinone | 14.18 | 100 | / | / |
| Picoxystrobin | 15.31 | 92.62 | / | / |
| Benziothiazolinone:picoxystrobin = 50:1 | 13.08 | 108.41 | 99.855 | 108.567 |
| Benziothiazolinone:picoxystrobin = 30:1 | 11.46 | 123.73 | 99.762 | 124.025 |
| Benziothiazolinone:picoxystrobin = 10:1 | 9.87 | 143.67 | 99.329 | 144.641 |
| Benziothiazolinone:picoxystrobin = 1:1 | 9.93 | 142.8 | 96.31 | 148.271 |
| Benziothiazolinone:picoxystrobin = 1:10 | 10.16 | 139.57 | 93.29 | 149.609 |
| Benziothiazolinone:picoxystrobin = 1:30 | 12.42 | 114.17 | 92.857 | 122.952 |
| Benziothiazolinone:picoxystrobin = 1:50 | 14.45 | 98.13 | 92.764 | 105.785 |

The results (in Table 9) show that the control effect of the combination of benziothiazolinone with picoxystrobin on downy mildew of grape is significantly improved, suggesting that the combination has an obvious synergistic effect on downy mildew pathogens of grape.

(10) Toxicity Test of Benziothiazolinone Combined with Fluazinam on Downy Mildew Pathogens of Grape

TABLE 10

Toxicity test result analysis of benziothiazolinone combined with fluazinam on downy mildew pathogens of grape

| Name of agent | $EC_{50}$ (μg/ml) | ATI | TTI | Co-toxicity coefficient (CTC) |
|---|---|---|---|---|
| Benziothiazolinone hydrochloride | 12.87 | 100 | / | / |
| Fluazinam | 11.24 | 114.5 | / | / |
| Benziothiazolinone:fluazinam = 50:1 | 11.16 | 115.32 | 100.284 | 114.993 |
| Benziothiazolinone:fluazinam = 30:1 | 10.22 | 125.93 | 100.468 | 125.343 |
| Benziothiazolinone:fluazinam = 10:1 | 8.27 | 155.62 | 101.318 | 153.596 |
| Benziothiazolinone:fluazinam = 1:1 | 7.81 | 164.79 | 107.251 | 153.649 |
| Benziothiazolinone:fluazinam = 1:10 | 8.12 | 158.5 | 113.183 | 140.039 |
| Benziothiazolinone:fluazinam = 1:30 | 9.18 | 140.2 | 114.034 | 122.946 |
| Benziothiazolinone:fluazinam = 1:50 | 10.45 | 123.16 | 114.217 | 107.830 |

The results (in Table 10) show that the control effect of the combination of benziothiazolinone with fluazinam on downy mildew of grape is significantly improved, suggesting that the combination has an obvious synergistic effect on downy mildew pathogens of grape.

2. Toxicity Test of Benziothiazolinone Combined Respectively with Pyraclostrobin, Boscalid, Benthiavalicarb-Isopropyl, Zoxamide, and Fenamidone on Late Blight Pathogens of Potato The test method was the same as above. (The test results are shown in Tables 11, 12, 13, 14, and 15 respectively)

(1) Toxicity Test of Benziothiazolinone Combined with Pyraclostrobin on Late Blight Pathogens of Potato

TABLE 11

Toxicity test result analysis of benziothiazolinone combined with pyraclostrobin on late blight pathogens of potato

| Name of agent | $EC_{50}$ (μg/ml) | ATI | TTI | Co-toxicity coefficient (CTC) |
|---|---|---|---|---|
| Benziothiazolinone | 6.89 | 100.00 | / | / |
| pyraclostrobin | 5.28 | 130.49 | / | / |
| Benziothiazolinone:pyraclostrobin = 50:1 | 5.72 | 120.45 | 100.598 | 119.74 |
| Benziothiazolinone:pyraclostrobin = 30:1 | 5.44 | 126.65 | 100.984 | 125.42 |
| Benziothiazolinone:pyraclostrobin = 10:1 | 4.63 | 148.81 | 102.772 | 144.80 |
| Benziothiazolinone:pyraclostrobin = 1:1 | 3.32 | 207.53 | 115.246 | 180.08 |
| Benziothiazolinone:pyraclostrobin = 1:10 | 2.93 | 235.15 | 127.720 | 184.12 |
| Benziothiazolinone:pyraclostrobin = 1:30 | 4.21 | 163.66 | 129.509 | 126.37 |
| Benziothiazolinone:pyraclostrobin = 1:50 | 4.68 | 147.22 | 129.895 | 113.34 |

The results (in Table 11) show that the control effect of the combination of benziothiazolinone with pyraclostrobin on late blight of potato is significantly improved, suggesting that the combination has an obvious synergistic effect on late blight pathogens of potato.

(2) Toxicity Test of Benziothiazolinone Combined with Boscalid on Late Blight Pathogens of Potato

TABLE 12

Toxicity test result analysis of benziothiazolinone combined with boscalid on late blight pathogens of potato

| Name of agent | $EC_{50}$ (μg/ml) | ATI | TTI | Co-toxicity coefficient (CTC) |
|---|---|---|---|---|
| Benziothiazolinone | 5.58 | 100.00 | / | / |
| Boscalid | 6.31 | 88.43 | / | / |
| Benziothiazolinone:boscalid = 50:1 | 4.78 | 116.74 | 99.7732 | 117.005 |
| Benziothiazolinone:boscalid = 30:1 | 4.62 | 120.78 | 99.6268 | 121.232 |
| Benziothiazolinone:boscalid = 10:1 | 4.21 | 132.54 | 98.9483 | 133.950 |
| Benziothiazolinone:boscalid = 1:1 | 3.28 | 170.12 | 94.2155 | 180.567 |
| Benziothiazolinone:boscalid = 1:10 | 3.18 | 175.47 | 89.4828 | 196.095 |
| Benziothiazolinone:boscalid = 1:30 | 4.91 | 113.65 | 88.8043 | 127.973 |
| Benziothiazolinone:boscalid = 1:50 | 5.55 | 100.54 | 88.6579 | 113.403 |

The results (in Table 12) show that the control effect of the combination of benziothiazolinone with boscalid on late blight of potato is significantly improved, suggesting that the combination has an obvious synergistic effect on late blight pathogens of potato.

(3) Toxicity Test of Benziothiazolinone Combined with Benthiavalicarb-Isopropyl on Late Blight Pathogens of Potato

TABLE 13

Toxicity test result analysis of benziothiazolinone combined with benthiavalicarb-isopropyl on late blight pathogens of potato

| Name of agent | $EC_{50}$ (μg/ml) | ATI | TTI | Co-toxicity coefficient (CTC) |
|---|---|---|---|---|
| Benziothiazolinone | 6.22 | 100.000 | / | / |
| Benthiavalicarb-isopropyl | 6.73 | 92.422 | / | / |
| Benziothiazolinone:benthiavalicarb-isopropyl = 50:1 | 5.43 | 114.549 | 99.851 | 114.719 |
| Benziothiazolinone:benthiavalicarb-isopropyl = 30:1 | 5.11 | 121.722 | 99.756 | 122.020 |
| Benziothiazolinone:benthiavalicarb-isopropyl = 10:1 | 4.17 | 149.161 | 99.311 | 150.195 |

TABLE 13-continued

Toxicity test result analysis of benziothiazolinone combined with benthiavalicarb-isopropyl on late blight pathogens of potato

| Name of agent | $EC_{50}$ (μg/ml) | ATI | TTI | Co-toxicity coefficient (CTC) |
|---|---|---|---|---|
| Benziothiazolinone:benthiavalicarb-isopropyl = 1:1 | 3.69 | 168.564 | 96.211 | 175.202 |
| Benziothiazolinone:benthiavalicarb-isopropyl = 1:10 | 4.25 | 146.353 | 93.111 | 157.181 |
| Benziothiazolinone:benthiavalicarb-isopropyl = 1:30 | 5.23 | 118.929 | 92.666 | 128.341 |
| Benziothiazolinone:benthiavalicarb-isopropyl = 1:50 | 5.61 | 110.873 | 92.571 | 119.772 |

The results (in Table 13) show that the control effect of the combination of benziothiazolinone with benthiavalicarb-isopropyl on late blight of potato is significantly improved, suggesting that the combination has an obvious synergistic effect on late blight pathogens of potato.

(4) Toxicity Test of Benziothiazolinone Combined with Zoxamide on Late Blight Pathogens of Potato

TABLE 14

Toxicity test result analysis of benziothiazolinone combined with zoxamide on late blight pathogens of potato

| Name of agent | $EC_{50}$ (μg/ml) | ATI | TTI | Co-toxicity coefficient (CTC) |
|---|---|---|---|---|
| Benziothiazolinone | 5.89 | 100.00 | / | / |
| Zoxamide | 6.21 | 94.85 | / | / |
| Benziothiazolinone:zoxamide = 50:1 | 5.21 | 113.05 | 99.899 | 113.164 |
| Benziothiazolinone:zoxamide = 30:1 | 4.82 | 122.2 | 99.834 | 122.403 |
| Benziothiazolinone:zoxamide = 10:1 | 4.09 | 144.01 | 99.532 | 144.687 |
| Benziothiazolinone:zoxamide = 1:1 | 3.58 | 164.53 | 97.424 | 168.880 |
| Benziothiazolinone:zoxamide = 1:10 | 4.05 | 145.43 | 95.315 | 152.578 |
| Benziothiazolinone:zoxamide = 1:30 | 5.21 | 113.05 | 95.013 | 118.984 |
| Benziothiazolinone:zoxamide = 1:50 | 5.42 | 108.67 | 94.948 | 114.452 |

The results (in Table 14) show that the control effect of the combination of benziothiazolinone with zoxamide on late blight of potato is significantly improved, suggesting that the combination has an obvious synergistic effect on late blight pathogens of potato.

(5) Toxicity Test of Benziothiazolinone Combined with Fenamidone on Late Blight Pathogens of Potato

TABLE 15

Toxicity test result analysis of benziothiazolinone combined with fenamidone on late blight pathogens of potato

| Name of agent | $EC_{50}$ (μg/ml) | ATI | TTI | Co-toxicity coefficient (CTC) |
|---|---|---|---|---|
| Benziothiazolinone | 6.12 | 100.00 | / | / |
| Fenamidone | 6.58 | 93.01 | / | / |
| Benziothiazolinone:fenamidone = 50:1 | 5.31 | 115.25 | 99.863 | 115.408 |
| Benziothiazolinone:fenamidone = 30:1 | 4.52 | 135.4 | 99.774 | 135.707 |
| Benziothiazolinone:fenamidone = 10:1 | 4.15 | 147.47 | 99.364 | 148.414 |
| Benziothiazolinone:fenamidone = 1:1 | 3.61 | 169.53 | 96.505 | 175.670 |
| Benziothiazolinone:fenamidone = 1:10 | 4.23 | 144.68 | 93.645 | 154.498 |
| Benziothiazolinone:fenamidone = 1:30 | 5.16 | 118.6 | 93.235 | 127.205 |
| Benziothiazolinone:fenamidone = 1:50 | 5.37 | 113.97 | 93.146 | 122.356 |

The results (in Table 15) show that the control effect of the combination of benziothiazolinone with fenamidone on late blight of potato is significantly improved, suggesting that the combination has an obvious synergistic effect on late blight pathogens of potato.

3. Toxicity Test of Benziothiazolinone Combined Respectively with Fluazinam, Prothioconazole, Picoxystrobin, Fluopicolide, and Famoxadone on Rust Pathogens of Wheat Test target organism: rust pathogens of wheat The test method was the same as above. (The test results are shown in Tables 16, 17, 18, 19, and 20 respectively)

(1) Toxicity Test of Benziothiazolinone Combined with Fluazinam on Rust Pathogens of Wheat

TABLE 16

Toxicity test result analysis of benziothiazolinone combined with fluazinam on rust pathogens of wheat

| Name of agent | $EC_{50}$ (μg/ml) | ATI | TTI | Co-toxicity coefficient (CTC) |
|---|---|---|---|---|
| Benziothiazolinone hydrochloride | 7.68 | 100 | / | / |
| Fluazinam | 8.15 | 94.23 | / | / |
| Benziothiazolinone:fluazinam = 50:1 | 6.82 | 112.61 | 99.887 | 112.737 |
| Benziothiazolinone:fluazinam = 30:1 | 6.41 | 119.81 | 99.814 | 120.033 |
| Benziothiazolinone:fluazinam = 10:1 | 5.68 | 135.21 | 99.476 | 135.922 |
| Benziothiazolinone:fluazinam = 1:1 | 5.21 | 147.41 | 97.117 | 151.786 |
| Benziothiazolinone:fluazinam = 1:10 | 5.56 | 138.13 | 94.757 | 145.773 |
| Benziothiazolinone:fluazinam = 1:30 | 6.46 | 118.89 | 94.419 | 125.917 |
| Benziothiazolinone:fluazinam = 1:50 | 6.87 | 111.79 | 94.346 | 118.489 |

The results (in Table 16) show that the control effect of the combination of benziothiazolinone with fluazinam on rust of wheat is significantly improved, suggesting that the combination has an obvious synergistic effect on rust pathogens of wheat.

(2) Toxicity Test of Benziothiazolinone Combined with Prothioconazole on Rust Pathogens of Wheat

TABLE 17

Toxicity test result analysis of benziothiazolinone combined with prothioconazole on rust pathogens of wheat

| Name of agent | $EC_{50}$ (μg/ml) | ATI | TTI | Co-toxicity coefficient (CTC) |
|---|---|---|---|---|
| Benziothiazolinone | 7.92 | 100 | / | / |
| Prothioconazole | 7.68 | 103.13 | / | / |
| Benziothiazolinone:prothioconazole = 50:1 | 7.11 | 111.39 | 100.061 | 111.322 |
| Benziothiazolinone:prothioconazole = 30:1 | 6.45 | 122.79 | 100.101 | 122.666 |
| Benziothiazolinone:prothioconazole = 10:1 | 5.61 | 141.18 | 100.284 | 140.780 |
| Benziothiazolinone:prothioconazole = 1:1 | 4.63 | 171.06 | 101.563 | 168.427 |
| Benziothiazolinone:prothioconazole = 1:10 | 5.27 | 150.28 | 102.841 | 146.128 |
| Benziothiazolinone:prothioconazole = 1:30 | 6.21 | 127.54 | 103.024 | 123.796 |
| Benziothiazolinone:prothioconazole = 1:50 | 6.62 | 119.64 | 103.064 | 116.083 |

The results (in Table 17) show that the control effect of the combination of benziothiazolinone with prothioconazole on rust of wheat is significantly improved, suggesting that the combination has an obvious synergistic effect on rust pathogens of wheat.

(3) Toxicity Test of Benziothiazolinone Combined with Picoxystrobin on Rust Pathogens of Wheat

TABLE 18

Toxicity test result analysis of benziothiazolinone combined with picoxystrobin on rust pathogens of wheat

| Name of agent | $EC_{50}$ (μg/ml) | ATI | TTI | Co-toxicity coefficient (CTC) |
|---|---|---|---|---|
| benziothiazolinone | 7.51 | 100 | / | / |
| picoxystrobin | 8.26 | 90.92 | / | / |
| benziothiazolinone:picoxystrobin = 50:1 | 6.52 | 115.18 | 99.822 | 115.385 |
| benziothiazolinone:picoxystrobin = 30:1 | 6.21 | 120.93 | 99.707 | 121.285 |
| benziothiazolinone:picoxystrobin = 10:1 | 5.48 | 137.04 | 99.175 | 138.180 |
| benziothiazolinone:picoxystrobin = 1:1 | 4.31 | 174.25 | 95.46 | 182.537 |
| benziothiazolinone:picoxystrobin = 1:10 | 5.18 | 144.98 | 91.746 | 158.023 |
| benziothiazolinone:picoxystrobin = 1:30 | 6.72 | 111.76 | 91.213 | 122.526 |
| benziothiazolinone:picoxystrobin = 1:50 | 6.98 | 107.59 | 91.098 | 118.104 |

The results (in Table 18) show that the control effect of the combination of benziothiazolinone with picoxystrobin on rust of wheat is significantly improved, suggesting that the combination has an obvious synergistic effect on rust pathogens of wheat.

(4) Toxicity Test of Benziothiazolinone Combined with Fluopicolide on Rust Pathogens of Wheat

TABLE 19

Toxicity test result analysis of benziothiazolinone combined with fluopicolide on rust pathogens of wheat

| Name of agent | $EC_{50}$ (μg/ml) | ATI | TTI | Co-toxicity coefficient (CTC) |
|---|---|---|---|---|
| Benziothiazolinone | 7.93 | 100 | / | / |
| Fluopicolide | 7.69 | 103.12 | / | / |
| Benziothiazolinone:fluopicolide = 50:1 | 6.98 | 113.61 | 100.061 | 113.541 |
| Benziothiazolinone:fluopicolide = 30:1 | 6.32 | 125.47 | 100.101 | 125.343 |
| Benziothiazolinone:fluopicolide = 10:1 | 5.26 | 150.76 | 100.284 | 150.333 |
| Benziothiazolinone:fluopicolide = 1:1 | 4.91 | 161.51 | 101.56 | 159.029 |
| Benziothiazolinone:fluopicolide = 1:10 | 5.32 | 149.06 | 102.837 | 144.948 |
| Benziothiazolinone:fluopicolide = 1:30 | 6.66 | 119.07 | 103.02 | 115.579 |
| Benziothiazolinone:fluopicolide = 1:50 | 6.85 | 115.77 | 103.06 | 112.333 |

The results (in Table 19) show that the control effect of the combination of benziothiazolinone with fluopicolide on rust of wheat is significantly improved, suggesting that the combination has an obvious synergistic effect on rust pathogens of wheat.

(5) Toxicity Test of Benziothiazolinone Combined with Famoxadone on Rust Pathogens of Wheat

TABLE 20

Toxicity test result analysis of benziothiazolinone combined with famoxadone on rust pathogens of wheat

| Name of agent | $EC_{50}$ (μg/ml) | ATI | TTI | Co-toxicity coefficient (CTC) |
|---|---|---|---|---|
| Benziothiazolinone | 7.51 | 100 | / | / |
| Famoxadone | 7.96 | 94.35 | / | / |
| Benziothiazolinone:famoxadone = 50:1 | 6.51 | 115.36 | 99.889 | 115.488 |
| Benziothiazolinone:famoxadone = 30:1 | 6.17 | 121.72 | 99.818 | 121.942 |
| Benziothiazolinone:famoxadone = 10:1 | 5.12 | 146.68 | 99.486 | 147.438 |
| Benziothiazolinone:famoxadone = 1:1 | 4.56 | 164.69 | 97.173 | 169.481 |
| Benziothiazolinone:famoxadone = 1:10 | 5.27 | 142.5 | 94.861 | 150.220 |
| Benziothiazolinone:famoxadone = 1:30 | 6.52 | 115.18 | 94.529 | 121.846 |
| Benziothiazolinone:famoxadone = 1:50 | 7.21 | 104.16 | 94.458 | 110.271 |

The results (in Table 20) show that the control effect of the combination of benziothiazolinone with famoxadone on rust of wheat is significantly improved, suggesting that the combination has an obvious synergistic effect on rust pathogens of wheat.

(II) Field Efficacy Test

Test method: in early stage of disease development, the first spray was given immediately, and then the second application was given after 7 days. Each treatment included 4 plots of 20 square meters each. The disease development before application and 10 days after the second application was statistically investigated. Samples were collected from 5 locations in each plot at random, and 5 plants were investigated at each location by investigating the percentages of the disease spot area on the leaves relative to the leaf area of the whole plant and grading. The disease index and the control effect were calculated.

$$\text{Disease index} = \frac{\sum \left( \begin{array}{c} \text{Number of leaves at each} \\ \text{grade of disease development} \times \\ \text{Representative value} \\ \text{of corresponding grade} \end{array} \right)}{\left( \begin{array}{c} \text{Total number of} \\ \text{leaves investigated} \end{array} \times \begin{array}{c} \text{Representative} \\ \text{value of highest level} \end{array} \right)} \times 100$$

Control effect (%) =

$$\left( 1 - \frac{\text{Disease index of control group before application} \times \text{Disease index of treatment group after application}}{\text{Disease index of control group after application} \times \text{Disease index of treatment group before application}} \right) \times 100$$

Anticipated control effect (%) = $X + Y - XY/100$ (where $X$ and $Y$ are the control effect of a single agent)

Grade Scale:

Grade 0: no disease spot;

Grade 1: number of disease spots on the leaf<5, and length<1 cm;

Grade 3: 6≤number of disease spots on the leaf≤10, and length of some disease spots>1 cm;

Grade 5: 11≤number of disease spots on the leaf≤25, some disease spots are contiguous, and the disease spot area is 10-25% of the leaf area;

Grade 7: number of disease spots on the leaf≥26, the disease spots are contiguous, and the disease spot area is 26-50% of the leaf area;

Grade 9: the disease spots are contiguous, and the disease spot area is above 50% of the leaf area, or all the leaves all wilted.

1. Field Efficacy Test of Benziothiazolinone Combined Respectively with Pyraclostrobin, Prothioconazole, Picoxystrobin, Fluopicolide, and Famoxadone for Controlling Wheat Powdery Mildew

TABLE 21

Field efficacy test of benziothiazolinone combined with the above fungicides for wheat powdery mildew

| No. | Treatment agent | Application rate (a.i.g/ha) | Disease index before application | Day 11 after the second application | |
|---|---|---|---|---|---|
| | | | | Disease index | Control effect (%) |
| Example 22 | 5% benziothiazolinone microemulsion | 145.2 | 4.02 | 7.51 | 75.2 |
| | 10% pyraclostrobin aqueous solution | 4.8 | 4.14 | 29.24 | 6.2 |
| | Anticipated control effect after mixing them | — | — | — | 76.7 |
| | 62% benziothiazolinone•pyraclostrobin wettable powder (benziothiazolinone:pyraclostrobin = 60:2) | 150 | 4.43 | 5.40 | 83.8 |
| Example 23 | 5% benziothiazolinone microemulsion | 75 | 4.72 | 20.19 | 43.2 |
| | 10% pyraclostrobin aqueous solution | 75 | 4.83 | 19.60 | 46.1 |
| | Anticipated control effect after mixing them | — | — | — | 69.4 |
| | 50% benziothiazolinone•pyraclostrobin wettable powder (benziothiazolinone:pyraclostrobin = 25:25) | 150 | 4.19 | 5.43 | 82.8 |
| Example 24 | 5% benziothiazolinone microemulsion | 4.8 | 4.6 | 33.22 | 4.1 |
| | 10% pyraclostrobin aqueous solution | 145.2 | 4.63 | 8.05 | 76.9 |
| | Anticipated control effect after mixing them | — | — | — | 77.8 |
| | 65% benziothiazolinone•pyraclostrobin wettable powder (benziothiazolinone:pyraclostrobin = 2:63) | 150 | 4.62 | 5.18 | 85.1 |
| Example 7 | 5% benziothiazolinone microemulsion | 145.2 | 4.46 | 9.10 | 72.9 |
| | 25% prothioconazole wettable powder | 4.8 | 4.79 | 34.20 | 5.2 |
| | Anticipated control effect after mixing them | — | — | — | 74.3 |
| | 62% benziothiazolinone•prothioconazole wettable powder (benziothiazolinone:prothioconazole = 60:2) | 150 | 4.74 | 5.07 | 85.8 |
| Example 8 | 5% benziothiazolinone microemulsion | 75 | 4.47 | 19.02 | 43.5 |
| | 25% prothioconazole wettable powder | 75 | 4.25 | 17.22 | 46.2 |
| | Anticipated control effect after mixing them | — | — | — | 69.6 |
| | 40% benziothiazolinone•prothioconazole wettable powder (benziothiazolinone:prothioconazole = 20:20) | 150 | 4.36 | 5.29 | 83.9 |

TABLE 21-continued

Field efficacy test of benziothiazolinone combined
with the above fungicides for wheat powdery mildew

| No. | Treatment agent | Application rate (a.i.g/ha) | Disease index before application | Day 11 after the second application | |
|---|---|---|---|---|---|
| | | | | Disease index | Control effect (%) |
| Example 9 | 5% benziothiazolinone microemulsion | 4.6 | 4.63 | 33.51 | 3.9 |
| | 25% prothioconazole wettable powder | 145.4 | 4.04 | 6.75 | 77.8 |
| | Anticipated control effect after mixing them | — | — | — | 78.7 |
| | 65% benziothiazolinone•prothioconazole wettable powder (benziothiazolinone:prothioconazole = 2:63) | 150 | 4.33 | 4.83 | 85.2 |
| Example 25 | 5% benziothiazolinone microemulsion | 145.4 | 4.17 | 7.66 | 75.6 |
| | 15% picoxystrobin concentrate | 4.6 | 4.02 | 28.79 | 4.9 |
| | Anticipated control effect after mixing them | — | — | — | 76.8 |
| | 65% benziothiazolinone•picoxystrobin wettable powder (benziothiazolinone:picoxystrobin = 63:2) | 150 | 4.23 | 4.84 | 84.8 |
| Example 26 | 5% benziothiazolinone microemulsion | 75 | 4.47 | 18.98 | 43.6 |
| | 15% picoxystrobin concentrate | 75 | 4.16 | 17.17 | 45.2 |
| | Anticipated control effect after mixing them | — | — | — | 69.1 |
| | 30% benziothiazolinone•picoxystrobin wettable powder (benziothiazolinone:picoxystrobin = 15:15) | 150 | 4.32 | 4.52 | 86.1 |
| Example 27 | 5% benziothiazolinone microemulsion | 4 | 4.42 | 31.99 | 3.9 |
| | 15% picoxystrobin concentrate | 146 | 4.03 | 6.92 | 77.2 |
| | Anticipated control effect after mixing them | — | — | — | 78.1 |
| | 75% benziothiazolinone•picoxystrobin wettable powder (benziothiazolinone:picoxystrobin = 2:73) | 150 | 4.02 | 4.21 | 86.1 |
| Example 16 | 5% benziothiazolinone microemulsion | 146 | 4.13 | 7.43 | 76.1 |
| | 10% fluopicolide suspension | 4 | 3.87 | 27.63 | 5.2 |
| | Anticipated control effect after mixing them | — | — | — | 77.3 |
| | 65% benziothiazolinone•fluopicolide wettable powder (benziothiazolinone:picoxystrobin = 63:2) | 150 | 3.81 | 4.33 | 84.9 |
| Example 17 | 5% benziothiazolinone microemulsion | 75 | 3.77 | 16.07 | 43.4 |
| | 10% fluopicolide suspension | 75 | 3.82 | 15.48 | 46.2 |
| | Anticipated control effect after mixing them | — | — | — | 69.5 |
| | 50% benziothiazolinone•fluopicolide wettable powder (benziothiazolinone:fluopicolide = 25:25) | 150 | 4.1 | 3.98 | 87.1 |
| Example 18 | 5% benziothiazolinone microemulsion | 4 | 4.23 | 30.58 | 4.0 |
| | 10% fluopicolide suspension | 146 | 4.02 | 7.54 | 75.1 |
| | Anticipated control effect after mixing them | — | — | — | 76.1 |
| | 65% benziothiazolinone•fluopicolide wettable powder | 150 | 4.43 | 5.07 | 84.8 |

TABLE 21-continued

Field efficacy test of benziothiazolinone combined with the above fungicides for wheat powdery mildew

| No. | Treatment agent | Application rate (a.i.g/ha) | Disease index before application | Day 11 after the second application Disease index | Control effect (%) |
|---|---|---|---|---|---|
| | (benziothiazolinone•fluopicolide = 2:63) | | | | |
| Example 19 | 5% benziothiazolinone microemulsion | 145 | 4.23 | 7.74 | 75.7 |
| | 30% famoxadone wettable powder | 5 | 4.8 | 33.91 | 6.2 |
| | Anticipated control effect after mixing them | — | — | — | 77.2 |
| | 60% benziothiazolinone•famoxadone wettable powder (benziothiazolinone:famoxadone = 58:2) | 150 | 4.42 | 4.63 | 86.1 |
| Example 20 | 5% benziothiazolinone microemulsion | 75 | 3.76 | 16.11 | 43.1 |
| | 30% famoxadone wettable powder | 75 | 3.89 | 15.76 | 46.2 |
| | Anticipated control effect after mixing them | — | — | — | 69.4 |
| | 50% benziothiazolinone•famoxadone wettable powder (benziothiazolinone:famoxadone = 25:25) | 150 | 4.06 | 4.34 | 85.8 |
| Example 21 | 5% benziothiazolinone microemulsion | 5 | 4.12 | 29.57 | 4.7 |
| | 30% famoxadone wettable powder | 150 | 4.33 | 8.09 | 75.2 |
| | Anticipated control effect after mixing them | — | — | — | 76.4 |
| | 60% benziothiazolinone•famoxadone wettable powder (benziothiazolinone:famoxadone = 2:58) | 150 | 4.3 | 4.50 | 86.1 |
| Water control (CK) | — | — | 3.28 | 24.7 | — |

The test results (in Table 21) show that the control effect of the combination of benziothiazolinone with pyraclostrobin, prothioconazole, picoxystrobin, fluopicolide, and famoxadone respectively on wheat powdery mildew is significantly improved, suggesting that the combination has an obvious synergistic effect on wheat powdery mildew.

(2) Field Efficacy Test of Benziothiazolinone Combined Respectively with Fluazinam, Boscalid, and Fluopicolide for Controlling Tomato Grey Mold

TABLE 22

Field efficacy test of benziothiazolinone or a salt thereof combined respectively with the above fungicides for tomato grey mold

| No. | Treatment agent | Application rate (a.i.g/ha) | Disease index before application | Day 11 after the second application Disease index | Control effect (%) |
|---|---|---|---|---|---|
| Example 28 | 5% benziothiazolinone microemulsion | 117 | 5.9 | 3.03 | 82.15 |
| | 12.5% fluazinam suspension | 3 | 6.23 | 17.42 | 2.95 |
| | Anticipated control effect after mixing them | — | — | — | 82.68 |
| | 62% benziothiazolinone•fluazinam wettable powder | 120 | 6.03 | 2.44 | 85.95 |

TABLE 22-continued

Field efficacy test of benziothiazolinone or a salt thereof combined respectively with the above fungicides for tomato grey mold

| No. | Treatment agent | Application rate (a.i.g/ha) | Disease index before application | Day 11 after the second application | |
|---|---|---|---|---|---|
| | | | | Disease index | Control effect (%) |
| | (benziothiazolinone:fluazinam = 60:2) | | | | |
| Example 29 | 5% benziothiazolinone microemulsion | 60 | 6.12 | 8.05 | 54.35 |
| | 12.5% fluazinam suspension | 60 | 6.23 | 10.42 | 41.95 |
| | Anticipated control effect after mixing them | — | — | — | 73.50 |
| | 40% benziothiazolinone•fluazinam wettable powder (benziothiazolinone:fluazinam = 20:20) | 120 | 6.25 | 2.28 | 87.35 |
| Example 30 | 5% benziothiazolinone microemulsion | 3.2 | 5.83 | 15.77 | 6.15 |
| | 12.5% fluazinam suspension | 116.8 | 5.78 | 4.12 | 75.25 |
| | Anticipated control effect after mixing them | — | — | — | 76.77 |
| | 75% benziothiazolinone carbonate•fluazinam wettable powder (benziothiazolinone:fluazinam = 2:73) | 120 | 5.89 | 2.49 | 85.35 |
| Example 10 | 5% benziothiazolinone microemulsion | 116.3 | 5.67 | 2.85 | 82.55 |
| | 20% boscalid aqueous emulsion | 3.7 | 5.83 | 16.25 | 3.25 |
| | Anticipated control effect after mixing them | — | — | — | 83.12 |
| | 65% benziothiazolinone•boscalid wettable powder (benziothiazolinone:boscalid = 63:2) | 120 | 5.7 | 2.24 | 86.35 |
| Example 11 | 5% benziothiazolinone microemulsion | 60 | 5.89 | 7.76 | 54.25 |
| | 20% boscalid aqueous emulsion | 60 | 6.23 | 9.43 | 47.45 |
| | Anticipated control effect after mixing them | — | — | — | 75.96 |
| | 60% benziothiazolinone•boscalid wettable powder (benziothiazolinone:boscalid = 30:30) | 120 | 5.9 | 2.17 | 87.25 |
| Example 12 | 5% benziothiazolinone microemulsion | 3.9 | 6.12 | 16.73 | 5.15 |
| | 20% boscalid aqueous emulsion | 116.1 | 5.78 | 4.12 | 75.25 |
| | Anticipated control effect after mixing them | — | — | — | 76.52 |
| | 62% benziothiazolinone•boscalid wettable powder (benziothiazolinone:boscalid = 2:60) | 120 | 6.03 | 2.46 | 85.85 |
| Example 16 | 5% benziothiazolinone microemulsion | 117.3 | 6.33 | 2.96 | 83.75 |
| | 30% fluopicolide aqueous emulsion | 2.8 | 6.33 | 17.83 | 2.25 |
| | Anticipated control effect after mixing them | — | — | — | 84.12 |
| | 65% benziothiazolinone•fluopicolide wettable powder (benziothiazolinone:fluopicolide = 63:2) | 120 | 6.23 | 2.49 | 86.15 |
| Example 17 | 5% benziothiazolinone microemulsion | 60 | 6.53 | 8.42 | 55.25 |
| | 30% fluopicolide aqueous emulsion | 60 | 6.14 | 9.05 | 48.85 |
| | Anticipated control effect after mixing them | — | — | — | 77.11 |
| | 50% benziothiazolinone•fluopicolide wettable powder (benziothiazolinone:fluopicolide = 25:25) | 120 | 6.16 | 2.60 | 85.35 |
| Example 18 | 5% benziothiazolinone microemulsion | 3.7 | 5.88 | 16.00 | 5.55 |
| | 30% fluopicolide aqueous emulsion | 116.3 | 5.9 | 2.95 | 82.65 |
| | Anticipated control effect after | — | — | — | 83.61 |

TABLE 22-continued

Field efficacy test of benziothiazolinone or a salt thereof combined respectively with the above fungicides for tomato grey mold

| | | | | Day 11 after the second application | |
|---|---|---|---|---|---|
| No. | Treatment agent | Application rate (a.i.g/ha) | Disease index before application | Disease index | Control effect (%) |
| | mixing them | | | | |
| | 65% benziothiazolinone•fluopicolide wettable powder (benziothiazolinone:fluopicolide = 2:63) | 120 | 6.06 | 2.38 | 86.35 |
| Water control (CK) | Water control | — | 6.08 | 17.52 | — |

The test results (in Table 22) show that the control effect of the combination of benziothiazolinone with fluazinam, boscalid, and fluopicolide respectively on tomato grey mold is significantly improved, suggesting that the combination has an obvious synergistic effect on tomato grey mold.

(3) Field Efficacy Test of Benziothiazolinone Combined Respectively with Benthiavalicarb-Isopropyl, Zoxamide, and Fenamidone for Controlling Grape Anthracnose

TABLE 23

Field efficacy test of benziothiazolinone combined respectively with the above fungicides for grape anthracnose

| | | | | Day 11 after the second application | |
|---|---|---|---|---|---|
| No. | Treatment agent | Application rate (a.i.g/ha) | Disease index before application | Disease index | Control effect (%) |
| Example 1 | 5% benziothiazolinone microemulsion | 130.2 | 3.89 | 4.65 | 83.1 |
| | 10% benthiavalicarb-isopropyl wettable powder | 4.8 | 3.98 | 26.83 | 4.6 |
| | Anticipated control effect after mixing them | — | — | — | 83.9 |
| | 62% benziothiazolinone•benthiavalicarb-isopropyl wettable powder (benziothiazolinone:benthiavalicarb-isopropyl = 60:2) | 135 | 3.87 | 3.77 | 86.2 |
| Example 2 | 5% benziothiazolinone microemulsion | 67.5 | 3.76 | 14.06 | 47.1 |
| | 10% benthiavalicarb-isopropyl wettable powder | 67.5 | 4.04 | 16.22 | 43.2 |
| | Anticipated control effect after mixing them | — | — | — | 70.0 |
| | 50% benziothiazolinone•benthiavalicarb-isopropyl wettable powder (benziothiazolinone:benthiavalicarb-isopropyl = 25:25) | 135 | 3.93 | 3.58 | 87.1 |
| Example 3 | 5% benziothiazolinone microemulsion | 3.6 | 3.87 | 25.38 | 7.2 |
| | 10% benthiavalicarb-isopropyl wettable powder | 131.4 | 3.87 | 5.96 | 78.2 |
| | Anticipated control effect after mixing them | — | — | — | 79.8 |
| | 65% benziothiazolinone•benthiayalicarb-isopropyl wettable powder (benziothiazolinone:benthiavalicarb-isopropyl = 2:63) | 135 | 3.94 | 3.87 | 86.1 |

TABLE 23-continued

Field efficacy test of benziothiazolinone combined respectively with the above fungicides for grape anthracnose

| No. | Treatment agent | Application rate (a.i.g/ha) | Disease index before application | Day 11 after the second application Disease index | Control effect (%) |
|---|---|---|---|---|---|
| Example 4 | 5% benziothiazolinone microemulsion | 130.6 | 3.65 | 4.62 | 82.1 |
| | 15% zoxamide wettable powder | 4.4 | 3.89 | 26.20 | 4.7 |
| | Anticipated control effect after mixing them | — | — | — | 82.9 |
| | 85% benziothiazolinone•zoxamide wettable powder (benziothiazolinone:zoxamide = 83:2) | 135 | 3.79 | 3.72 | 86.1 |
| Example 5 | 5% benziothiazolinone microemulsion | 67.5 | 3.78 | 14.00 | 47.6 |
| | 15% zoxamide wettable powder | 67.5 | 3.85 | 15.10 | 44.5 |
| | Anticipated control effect after mixing them | — | — | — | 70.9 |
| | 30% benziothiazolinone•zoxamide wettable powder (benziothiazolinone:zoxamide = 15:15) | 135 | 3.91 | 3.81 | 86.2 |
| Example 6 | 5% benziothiazolinone microemulsion | 4.2 | 3.86 | 25.12 | 7.9 |
| | 15% zoxamide wettable powder | 130.8 | 3.82 | 5.37 | 80.1 |
| | Anticipated control effect after mixing them | — | — | — | 81.7 |
| | 75% benziothiazolinone•zoxamide wettable powder benziothiazolinone:zoxamide = 2:73) | 135 | 3.79 | 3.96 | 85.2 |
| Example 13 | 5% benziothiazolinone microemulsion | 131.8 | 3.91 | 5.44 | 80.3 |
| | 20% fenamidone wettable powder | 3.2 | 3.21 | 21.57 | 4.9 |
| | Anticipated control effect after mixing them | — | — | — | 81.3 |
| | 62% benziothiazolinone•fenamidone wettable powder (benziothiazolinone:fenamidone = 60:2) | 135 | 3.79 | 3.80 | 85.8 |
| Example 14 | 5% benziothiazolinone microemulsion | 67.5 | 3.98 | 14.60 | 48.1 |
| | 20% fenamidone wettable powder | 67.5 | 4.05 | 15.31 | 46.5 |
| | Anticipated control effect after mixing them | — | — | — | 72.2 |
| | 50% benziothiazolinone•fenamidone wettable powder (benziothiazolinone:fenamidone = 25:25) | 135 | 3.99 | 3.33 | 88.2 |
| Example 15 | 5% benziothiazolinone microemulsion | 3.5 | 3.73 | 24.49 | 7.1 |
| | 20% fenamidone wettable powder | 131.5 | 3.32 | 4.62 | 80.3 |
| | Anticipated control effect after mixing them | — | — | — | 81.7 |
| | 62% benziothiazolinone•fenamidone wettable powder (benziothiazolinone:fenamidone = 2:60) | 135 | 3.54 | 3.38 | 86.5 |
| Water control (CK) | — | — | 3.87 | 27.35 | — |

The test results (in Table 23) show that the control effect of the combination of benziothiazolinone with benthiavalicarb-isopropyl, zoxamide, and fenamidone respectively on grape anthracnose is significantly improved, suggesting that the combination has an obvious synergistic effect on grape anthracnose.

What is claimed is:

1. A fungicidal composition having a synergistic effect, comprising active ingredients A and B, wherein:
the active ingredient A is benziothiazolinone,
the active ingredient B is one selected from the group consisting of benthiavalicarb-isopropyl, zoxamide, prothioconazole, boscalid, fluopicolide and fluazinam, and
the weight ratio of the two ingredients is from 1:30 to 30:1.

2. The fungicidal composition according to claim 1, wherein the weight ratio of the active ingredient A to the active ingredient B is from 1:20 to 20:1.

3. The fungicidal composition according to claim 1, wherein the weight ratio of the active ingredient A to the active ingredient B is from 1:10 to 30:1.

4. The fungicidal composition according to claim 1, comprising 5-85% by weight of the active ingredients and 95-15% by weight of pesticide adjuvants.

5. The fungicidal composition according to claim 4, which is prepared into pesticidally acceptable formations with the active ingredients and the pesticide adjuvants.

6. The fungicidal composition according to claim 5, which is in the form of a wettable powder prepared with the active ingredients and the pesticide adjuvants.

7. The fungicidal composition according to claim 1 is used in the control of diseases on crops in the agricultural area.

8. The fungicidal composition according to claim 1 is used in the control of grape downy mildew, wheat rust, potato late blight, wheat powdery mildew, tomato grey mold or grape anthracnose.

9. The fungicidal composition according to claim 2 is used in the control of diseases on crops in the agricultural area.

10. The fungicidal composition according to claim 3 is used in the control of diseases on crops in the agricultural area.

11. The fungicidal composition according to claim 2 is used in the control of grape downy mildew, wheat rust, potato late blight, wheat powdery mildew, tomato grey mold or grape anthracnose.

12. The fungicidal composition according to claim 3 is used in the control of grape downy mildew, wheat rust, potato late blight, wheat powdery mildew, tomato grey mold or grape anthracnose.

13. The fungicidal composition according to claim 1, wherein the active ingredient B is selected from the group consisting of benthiavalicarb-isopropyl, zoxamide, and prothioconazole.

14. The fungicidal composition according to claim 1, wherein the active ingredient B is selected from the group consisting of boscalid, fluopicolide, and fluazinam.

15. The fungicidal composition according to claim 1, wherein the active ingredient B is fluopicolide.

16. The fungicidal composition according to claim 1, wherein the active ingredient B is selected from the group consisting of boscalid and fluazinam.

17. The fungicidal composition according to claim 1, wherein the active ingredient B is prothioconazole.

* * * * *